US011155697B2

(12) United States Patent
Gane et al.

(10) Patent No.: US 11,155,697 B2
(45) Date of Patent: *Oct. 26, 2021

(54) PROCESS FOR THE PRODUCTION OF GEL-BASED COMPOSITE MATERIALS

(75) Inventors: Patrick A. C. Gane, Rothrist (CH); Michel Schenker, Oftringen (CH); Ramjee Subramanian, Bangalore (IN); Joachim Schölkopf, Killwangen (CH)

(73) Assignee: FiberLean Technologies Limited, Par Cornwall (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/640,513

(22) PCT Filed: Apr. 26, 2011

(86) PCT No.: PCT/EP2011/056540
§ 371 (c)(1),
(2), (4) Date: Jan. 16, 2013

(87) PCT Pub. No.: WO2011/134938
PCT Pub. Date: Nov. 3, 2011

(65) Prior Publication Data
US 2013/0131193 A1 May 23, 2013

Related U.S. Application Data

(60) Provisional application No. 61/343,774, filed on May 4, 2010.

(30) Foreign Application Priority Data

Apr. 27, 2010 (EP) .................................. 10161173

(51) Int. Cl.
D21H 11/18 (2006.01)
C08L 1/02 (2006.01)
D21H 17/67 (2006.01)
D21C 9/00 (2006.01)
D21H 17/64 (2006.01)
A61P 17/02 (2006.01)
D21H 21/18 (2006.01)
D21H 17/00 (2006.01)

(52) U.S. Cl.
CPC .................. C08L 1/02 (2013.01); A61P 17/02 (2018.01); D21C 9/007 (2013.01); D21H 11/18 (2013.01); D21H 17/64 (2013.01); D21H 17/675 (2013.01); D21H 17/74 (2013.01); D21H 21/18 (2013.01)

(58) Field of Classification Search
USPC ...................................................... 162/181.2
See application file for complete search history.

(56) References Cited

U.S. PATENT DOCUMENTS

| 57,307 A | 8/1866 | Fletcher |
| 168,783 A | 10/1875 | Riley |
| 1,538,257 A | 5/1925 | Obrecht |
| 2,006,209 A | 5/1933 | Bradner |
| 2,169,473 A | 8/1939 | Olsen |
| 2,583,548 A | 1/1952 | Lutton |
| 3,075,710 A | 1/1963 | Feld et al. |
| 3,730,830 A | 5/1973 | Driscoll |
| 3,765,921 A | 10/1973 | Puskar |
| 3,794,558 A | 2/1974 | Back |
| 3,820,548 A | 6/1974 | Buchmann et al. |
| 3,921,581 A | 11/1975 | Brewer |
| 4,026,762 A | 5/1977 | Bauman |
| 4,087,317 A | 5/1978 | Roberts |
| 4,167,548 A | 9/1979 | Arduini et al. |
| 4,229,250 A | 10/1980 | Lehtinen |
| 4,275,084 A | 6/1981 | Ohyabu et al. |
| 4,285,842 A | 8/1981 | Herr |
| 4,318,959 A | 3/1982 | Evans et al. |
| 4,341,807 A | 7/1982 | Turbak et al. |
| 4,356,060 A | 10/1982 | Neckermann et al. |
| 4,374,702 A | 2/1983 | Turbak et al. |
| 4,378,381 A | 3/1983 | Turback et al. |
| 4,426,258 A | 1/1984 | Browning |
| 4,452,721 A | 6/1984 | Turback et al. |
| 4,452,722 A | 6/1984 | Turback et al. |
| 4,460,737 A | 8/1984 | Evans et al. |
| 4,464,287 A | 8/1984 | Turback et al. |

(Continued)

FOREIGN PATENT DOCUMENTS

| BE | 1006908 A3 | 1/1995 |
| CA | 1096676 A | 3/1981 |

(Continued)

OTHER PUBLICATIONS

International Search Report, dated Jun. 22, 2011 for PCT Application No. PCT/EP2011/056540.

(Continued)

Primary Examiner — Mark Halpern
(74) Attorney, Agent, or Firm — Raymond G. Arner; Pierce Atwood LLP

(57) ABSTRACT

A process for the production of composite materials comprising nano-fibrillar cellulose gels, by providing cellulose fibres and at least one filler and/or pigment, combining the cellulose fibres and the at least one filler and/or pigment, fibrillating the cellulose fibres in the presence of the at least one filler and/or pigment until a gel is formed, subsequently providing at least one further filler and/or pigment and combining the gel with the at least one further filler and/or pigment.

22 Claims, No Drawings

(56) References Cited

U.S. PATENT DOCUMENTS

| | | | |
|---|---|---|---|
| 4,474,949 | A | 10/1984 | Chatterjee et al. |
| 4,481,076 | A | 11/1984 | Herrick |
| 4,481,077 | A | 11/1984 | Herrick et al. |
| 4,487,634 | A | 12/1984 | Turkback et al. |
| 4,495,245 | A * | 1/1985 | Zunker .................. 428/403 |
| 4,500,546 | A | 2/1985 | Turback et al. |
| 4,510,020 | A | 4/1985 | Green et al. |
| 4,705,712 | A | 11/1987 | Cashaw et al. |
| 4,744,987 | A | 5/1988 | Mehra et al. |
| 4,761,203 | A | 8/1988 | Vinson |
| 4,820,813 | A | 4/1989 | Schultz |
| 4,889,594 | A | 12/1989 | Gavelin |
| 4,952,278 | A | 8/1990 | Gregory et al. |
| 5,009,886 | A | 4/1991 | Ahmad et al. |
| 5,098,520 | A | 3/1992 | Begala |
| 5,104,411 | A | 4/1992 | Makoui et al. |
| 5,123,962 | A | 6/1992 | Komuro et al. |
| 5,156,719 | A | 10/1992 | Passaretti |
| 5,223,090 | A | 6/1993 | Klungness et al. |
| 5,227,024 | A | 6/1993 | Gomez |
| 5,225,041 | A | 7/1993 | Richard et al. |
| 5,228,900 | A | 7/1993 | Stephens et al. |
| 5,240,561 | A | 8/1993 | Kaliski |
| 5,244,542 | A | 9/1993 | Bown et al. |
| 5,269,470 | A | 12/1993 | Ishikawa et al. |
| 5,274,199 | A | 12/1993 | Uryu et al. |
| 5,279,663 | A | 1/1994 | Kaliski |
| 5,312,484 | A | 1/1994 | Kaliski |
| 5,290,830 | A | 3/1994 | Tung et al. |
| 5,316,621 | A | 5/1994 | Kitao et al. |
| 5,385,640 | A | 1/1995 | Weibel et al. |
| 5,443,902 | A | 1/1995 | Knox et al. |
| 5,387,319 | A | 2/1995 | Mora et al. |
| 5,487,419 | A | 1/1996 | Weibel |
| 5,531,821 | A * | 7/1996 | Wu .................. 106/464 |
| 5,605,568 | A | 2/1997 | Naydowski et al. |
| 5,670,623 | A | 9/1997 | Shoseyov et al. |
| 5,731,080 | A | 3/1998 | Cousin et al. |
| 5,840,320 | A | 3/1998 | Odom |
| 5,817,381 | A | 11/1998 | Chen et al. |
| 5,837,376 | A | 11/1998 | Knox et al. |
| 5,964,983 | A | 10/1999 | Dinand et al. |
| 6,037,380 | A | 3/2000 | Venables et al. |
| 6,074,524 | A | 6/2000 | Wu et al. |
| 6,083,317 | A | 7/2000 | Snowden et al. |
| 6,083,582 | A | 7/2000 | Chen et al. |
| 6,117,305 | A | 9/2000 | Bando et al. |
| 6,117,474 | A | 9/2000 | Kamada et al. |
| 6,117,545 | A | 9/2000 | Cavaille et al. |
| 6,117,804 | A | 9/2000 | Cho |
| 6,132,558 | A | 10/2000 | Dyllick-Brenzinger et al. |
| 6,156,118 | A | 12/2000 | Silenius |
| 6,159,335 | A | 12/2000 | Owens et al. |
| 6,183,596 | B1 * | 2/2001 | Matsuda et al. .................. 162/9 |
| 6,202,946 | B1 | 3/2001 | Virtanen |
| 6,207,436 | B1 | 3/2001 | Bjørnvad et al. |
| 6,214,163 | B1 | 4/2001 | Matsuda et al. |
| 6,235,150 | B1 | 5/2001 | Middleton et al. |
| 6,312,669 | B1 | 11/2001 | Cantiani et al. |
| 6,339,898 | B1 | 1/2002 | Toye |
| 6,379,594 | B1 | 4/2002 | Dopfner et al. |
| 6,436,232 | B1 | 8/2002 | Silenius et al. |
| 6,468,393 | B1 | 10/2002 | Small et al. |
| 6,579,410 | B1 | 6/2003 | Bleakley et al. |
| 6,604,698 | B2 | 8/2003 | Verhoff et al. |
| 6,647,662 | B2 | 11/2003 | Toye |
| 6,669,882 | B2 | 12/2003 | Seok |
| 6,706,876 | B2 | 3/2004 | Luo et al. |
| 6,726,807 | B1 | 4/2004 | Mathur |
| 6,787,497 | B2 | 9/2004 | Dellve et al. |
| 6,861,081 | B2 | 3/2005 | Weibel |
| 7,022,756 | B2 | 4/2006 | Singer |
| 7,048,900 | B2 | 5/2006 | Mathur et al. |
| 7,083,703 | B2 | 8/2006 | Aho et al. |
| 7,169,258 | B2 | 1/2007 | Rheims et al. |
| 7,179,347 | B2 | 2/2007 | Rheims et al. |
| 7,285,182 | B2 | 10/2007 | Mason et al. |
| 7,381,294 | B2 | 6/2008 | Suzuki et al. |
| 7,459,493 | B2 | 12/2008 | Singer |
| 7,462,232 | B2 | 12/2008 | Tuason et al. |
| 7,497,924 | B2 | 3/2009 | Nguyen et al. |
| 7,594,619 | B2 | 9/2009 | Ghere, Jr. et al. |
| 7,726,592 | B2 | 6/2010 | Fernandez et al. |
| 7,790,276 | B2 | 9/2010 | Kanakarajan |
| 7,799,358 | B2 | 9/2010 | Weibel |
| 8,012,312 | B2 | 9/2011 | Goto et al. |
| 8,012,573 | B2 | 9/2011 | Kowata et al. |
| 8,231,764 | B2 | 7/2012 | Husband et al. |
| 8,871,056 | B2 | 10/2014 | Gane et al. |
| 8,871,057 | B2 | 10/2014 | Gane et al. |
| 9,157,189 | B2 | 10/2015 | Heiskanen et al. |
| 9,175,442 | B2 | 11/2015 | Gane et al. |
| 9,399,838 | B2 | 7/2016 | Laine et al. |
| 2001/0011516 | A1 | 8/2001 | Cantiani et al. |
| 2001/0045264 | A1 | 11/2001 | Rheims et al. |
| 2002/0031592 | A1 | 3/2002 | Weibel |
| 2002/0059886 | A1 | 5/2002 | Merkley et al. |
| 2002/0198293 | A1 | 12/2002 | Craun et al. |
| 2003/0051841 | A1 | 3/2003 | Mathur et al. |
| 2003/0094252 | A1 * | 5/2003 | Sundar et al. .................. 162/128 |
| 2003/0114641 | A1 | 6/2003 | Kelly et al. |
| 2004/0108081 | A1 | 6/2004 | Hughes |
| 2004/0131854 | A1 | 7/2004 | Aho et al. |
| 2004/0146605 | A1 | 7/2004 | Weibel |
| 2004/0149403 | A1 | 8/2004 | Rheims et al. |
| 2004/0168782 | A1 | 9/2004 | Silenius et al. |
| 2004/0168783 | A1 | 9/2004 | Munchow |
| 2004/0173329 | A1 | 9/2004 | Silenius et al. |
| 2004/0226671 | A1 | 11/2004 | Nguyen et al. |
| 2005/0000665 | A1 | 1/2005 | Doelle |
| 2005/0045288 | A1 | 3/2005 | Riou |
| 2005/0051054 | A1 | 3/2005 | White et al. |
| 2005/0089601 | A1 | 4/2005 | Weibel |
| 2005/0103459 | A1 | 5/2005 | Mathur |
| 2005/0116010 | A1 * | 6/2005 | Gronroos et al. ............ 228/101 |
| 2005/0133643 | A1 | 6/2005 | Fernandez et al. |
| 2005/0194477 | A1 | 9/2005 | Suzuki |
| 2005/0256262 | A1 | 11/2005 | Hill et al. |
| 2006/0078647 | A1 | 4/2006 | Weibel |
| 2006/0201646 | A1 | 9/2006 | Gussinyer Canadell |
| 2006/0266485 | A1 | 11/2006 | Knox et al. |
| 2006/0280839 | A1 | 12/2006 | Weibel |
| 2006/0289132 | A1 | 12/2006 | Heijnesson-Hulten |
| 2007/0062009 | A1 | 3/2007 | Ghere, Jr. et al. |
| 2007/0131361 | A1 | 6/2007 | Doelle et al. |
| 2007/0148365 | A1 | 6/2007 | Knox et al. |
| 2007/0224419 | A1 | 9/2007 | Sumnicht et al. |
| 2007/0226919 | A1 | 10/2007 | Mheidle |
| 2007/0231568 | A1 | 10/2007 | Kanakarajan |
| 2007/0272376 | A1 | 11/2007 | Maijala et al. |
| 2008/0023161 | A1 | 1/2008 | Gather |
| 2008/0057307 | A1 | 3/2008 | Koslow et al. |
| 2008/0060774 | A1 | 3/2008 | Zuraw et al. |
| 2008/0146701 | A1 | 6/2008 | Sain et al. |
| 2008/0210391 | A1 | 9/2008 | Pfalzer et al. |
| 2008/0265222 | A1 | 10/2008 | Ozersky et al. |
| 2009/0020139 | A1 | 1/2009 | Sumnicht et al. |
| 2009/0020248 | A1 | 1/2009 | Sumnicht et al. |
| 2009/0065164 | A1 | 3/2009 | Goto et al. |
| 2009/0084874 | A1 | 4/2009 | Alam et al. |
| 2009/0221812 | A1 | 9/2009 | Ankerfors et al. |
| 2010/0024998 | A1 | 2/2010 | Wildlock et al. |
| 2010/0059191 | A1 | 3/2010 | Garcia Melgarejo et al. |
| 2010/0132901 | A1 | 6/2010 | Wild |
| 2010/0139527 | A1 | 6/2010 | Fernandez-Garcia |
| 2010/0212850 | A1 | 8/2010 | Sumnicht et al. |
| 2010/0233468 | A1 | 9/2010 | Ioelovich et al. |
| 2010/0272938 | A1 | 10/2010 | Mitchell et al. |
| 2010/0272980 | A1 | 10/2010 | Kowata et al. |
| 2011/0081554 | A1 | 4/2011 | Ankerfors et al. |
| 2011/0088860 | A1 | 4/2011 | Heijnesson-Hulten et al. |
| 2011/0114765 | A1 | 5/2011 | Brady et al. |
| 2011/0186252 | A1 | 8/2011 | Subramanian et al. |
| 2011/0223401 | A1 | 9/2011 | Harlin et al. |

(56) References Cited

U.S. PATENT DOCUMENTS

| | | |
|---|---|---|
| 2011/0259537 A1 | 10/2011 | Husband et al. |
| 2011/0274908 A1 | 11/2011 | Kowata et al. |
| 2011/0277947 A1 | 11/2011 | Hua et al. |
| 2012/0043039 A1 | 2/2012 | Paltakari et al. |
| 2012/0094953 A1 | 4/2012 | Gane et al. |
| 2012/0107480 A1 | 5/2012 | Gane et al. |
| 2012/0125547 A1 | 5/2012 | Akai et al. |
| 2012/0132383 A1 | 5/2012 | Laine et al. |
| 2012/0205065 A1 | 8/2012 | Esser |
| 2012/0216718 A1 | 8/2012 | Berglund et al. |
| 2012/0277351 A1 | 11/2012 | Yano et al. |
| 2012/0318471 A1 | 12/2012 | Turkki et al. |
| 2013/0000855 A1 | 1/2013 | Nuopponen et al. |
| 2013/0017349 A1 | 1/2013 | Heiskanen et al. |
| 2013/0053454 A1 | 2/2013 | Heiskanen et al. |
| 2013/0126112 A1 | 5/2013 | Gane et al. |
| 2013/0131193 A1 | 5/2013 | Gane et al. |
| 2013/0133848 A1 | 5/2013 | Heijnesson-Hulten et al. |
| 2013/0180680 A1 | 7/2013 | Axrup et al. |
| 2013/0190680 A1 | 7/2013 | Axrup et al. |
| 2013/0284387 A1 | 10/2013 | Umemoto et al. |
| 2013/0345416 A1 | 12/2013 | Laukkanen et al. |
| 2014/0058077 A1 | 2/2014 | Laukkanen et al. |
| 2014/0302337 A1 | 10/2014 | Gane et al. |
| 2014/0345816 A1 | 11/2014 | Heiskanen et al. |
| 2014/0370179 A1 | 12/2014 | Gane et al. |
| 2014/0371172 A1 | 12/2014 | Gane et al. |
| 2015/0101769 A1 | 4/2015 | Laine et al. |
| 2015/0101770 A1 | 4/2015 | Laine et al. |
| 2015/0144279 A1 | 5/2015 | Laine et al. |
| 2015/0330024 A1 | 11/2015 | Gane et al. |
| 2016/0273165 A1 | 9/2016 | Laine et al. |
| 2016/0299119 A1 | 10/2016 | Laukkanen et al. |

FOREIGN PATENT DOCUMENTS

| | | |
|---|---|---|
| CA | 1149219 A | 7/1983 |
| CA | 1162819 A | 2/1984 |
| CA | 2292587 A1 | 12/1998 |
| CA | 2093545 C | 3/2001 |
| CA | 2 437 616 A1 | 2/2005 |
| CA | 2750082 A1 | 8/2010 |
| CH | 648071 A5 | 2/1985 |
| CN | 85108131 A | 5/1987 |
| CN | 1089675 A | 7/1994 |
| CN | 1173904 A | 2/1998 |
| CN | 1200128 A | 11/1998 |
| CN | 1278830 A | 1/2001 |
| CN | 2437616 Y | 7/2001 |
| CN | 1524145 A | 8/2004 |
| CN | 1585839 A1 | 2/2005 |
| CN | 101360863 A | 2/2005 |
| CN | 1665984 A | 9/2005 |
| CN | 101203644 A | 6/2008 |
| CN | 102869831 B1 | 9/2015 |
| DK | 175143 B1 | 6/2004 |
| EP | 51230 A1 | 5/1982 |
| EP | 39628 B1 | 7/1984 |
| EP | 0198622 A1 | 10/1986 |
| EP | 273745 A2 | 7/1988 |
| EP | 442183 A1 | 8/1991 |
| EP | 492600 A1 | 7/1992 |
| EP | 499578 A1 | 8/1992 |
| EP | 0614948 A1 | 9/1994 |
| EP | 619140 A2 | 10/1994 |
| EP | 0625611 A1 | 11/1994 |
| EP | 0726356 A1 | 8/1996 |
| EP | 579171 B1 | 1/1997 |
| EP | 785307 A2 | 7/1997 |
| EP | 790135 A2 | 8/1997 |
| EP | 619140 B1 | 5/1999 |
| EP | 0935020 A1 | 8/1999 |
| EP | 0949294 A1 | 10/1999 |
| EP | 988322 B1 | 1/2002 |
| EP | 1053213 B1 | 5/2002 |
| EP | 785307 B1 | 9/2002 |
| EP | 0852588 B1 | 1/2003 |
| EP | 1469126 A1 | 10/2004 |
| EP | 1 538 257 A1 | 6/2005 |
| EP | 1936032 A1 | 6/2008 |
| EP | 2196579 A1 | 6/2010 |
| EP | 2216345 A1 | 8/2010 |
| EP | 2236545 A1 | 10/2010 |
| EP | 2236664 A1 | 10/2010 |
| EP | 1907626 B1 | 11/2010 |
| EP | 2386682 B1 | 11/2011 |
| EP | 2386683 B1 | 3/2014 |
| EP | 2563967 B1 | 8/2017 |
| EP | 2640893 B1 | 8/2017 |
| ES | 2100781 A1 | 6/1997 |
| FR | 2689530 A1 | 10/1993 |
| FR | 2774702 A1 | 8/1999 |
| GB | 663 621 | 12/1951 |
| GB | 663621 | 12/1951 |
| GB | 663621 A | 12/1951 |
| GB | 2260146 A | 4/1993 |
| GB | 2265916 A | 10/1993 |
| GB | 2275876 A | 9/1994 |
| GB | 2528487 A | 1/2016 |
| JP | 1-156587 A | 6/1989 |
| JP | H04-81813 A | 7/1992 |
| JP | H5098589 A | 4/1993 |
| JP | 6-158585 A | 6/1994 |
| JP | 06-240588 A | 8/1994 |
| JP | 08081896 A | 3/1996 |
| JP | 2528487 B2 | 8/1996 |
| JP | 8-284090 A | 10/1996 |
| JP | 9-124702 A | 5/1997 |
| JP | 10-158303 A | 6/1998 |
| JP | 10237220 A | 9/1998 |
| JP | 10237220 A | 9/1998 |
| JP | 11-269796 A | 10/1999 |
| JP | 2976485 B2 | 11/1999 |
| JP | 2981555 B1 | 11/1999 |
| JP | 2000-170029 A | 6/2000 |
| JP | 3421446 B2 | 6/2003 |
| JP | 2004-231796 A | 8/2004 |
| JP | 2004-523676 A | 8/2004 |
| JP | 2004-534911 A | 11/2004 |
| JP | 2005-505708 A | 2/2005 |
| JP | 2006-008857 A | 1/2006 |
| JP | 2007-262594 A | 10/2007 |
| JP | 2008007899 A | 1/2008 |
| JP | 2008-150719 A | 7/2008 |
| JP | 2008-169497 A | 7/2008 |
| JP | 2009-161613 A | 7/2009 |
| JP | 2009-243014 A | 10/2009 |
| JP | 2009-263854 A | 11/2009 |
| JP | 2010-168716 A | 8/2010 |
| JP | 2010-202987 A | 9/2010 |
| JP | 2012-522145 A | 9/2012 |
| JP | 5666553 B2 | 2/2015 |
| JP | 5894525 B2 | 3/2016 |
| KR | 2008-0096747 A | 11/2008 |
| NL | 8102857 A | 1/1983 |
| RU | 2208079 C2 | 7/2003 |
| RU | 2345189 C2 | 1/2009 |
| RU | 2011143854 A | 5/2013 |
| SU | 499366 A1 | 1/1977 |
| TW | 200609278 A | 3/2006 |
| TW | 201013017 A1 | 4/2010 |
| WO | 93/01333 A1 | 1/1993 |
| WO | 9315270 A1 | 8/1993 |
| WO | 94/05595 A1 | 3/1994 |
| WO | 9404745 A1 | 3/1994 |
| WO | 97/12917 A1 | 4/1997 |
| WO | 9712917 A1 | 4/1997 |
| WO | 9718897 A2 | 5/1997 |
| WO | 98/28362 A1 | 7/1998 |
| WO | 98/55693 A1 | 12/1998 |
| WO | 98/56826 A1 | 12/1998 |
| WO | 9856860 A1 | 12/1998 |
| WO | 199856860 | 12/1998 |
| WO | 99/54045 A1 | 10/1999 |

(56) References Cited

FOREIGN PATENT DOCUMENTS

| | | |
|---|---|---|
| WO | 01/66600 A1 | 9/2001 |
| WO | 01/98231 A1 | 12/2001 |
| WO | 02/086238 A1 | 10/2002 |
| WO | 02/090651 A1 | 11/2002 |
| WO | 02090651 A1 | 11/2002 |
| WO | 02/100955 A1 | 12/2002 |
| WO | 02100955 A1 | 12/2002 |
| WO | 03033815 A2 | 4/2003 |
| WO | 2003033815 A2 | 4/2003 |
| WO | 2004/016852 A1 | 2/2004 |
| WO | 2004/055267 A1 | 7/2004 |
| WO | 2005014934 A2 | 2/2005 |
| WO | 2005/061793 A1 | 7/2005 |
| WO | 2005/100489 A1 | 10/2005 |
| WO | 2005/123840 A1 | 12/2005 |
| WO | 2006/009502 A1 | 1/2006 |
| WO | 2006/041401 A1 | 4/2006 |
| WO | 2006/136651 A1 | 12/2006 |
| WO | 2007/006794 A1 | 1/2007 |
| WO | 2007/088974 A1 | 8/2007 |
| WO | 2007/091942 A1 | 8/2007 |
| WO | 2007/096180 A2 | 8/2007 |
| WO | 2007/110639 A1 | 10/2007 |
| WO | 2008/008576 A2 | 1/2008 |
| WO | 2008/033283 A1 | 3/2008 |
| WO | 2008/076056 A1 | 6/2008 |
| WO | 2008/076071 A1 | 6/2008 |
| WO | 2008/095764 A1 | 8/2008 |
| WO | 2008/132228 A1 | 11/2008 |
| WO | 2009/074491 A1 | 6/2009 |
| WO | 2009/122982 A1 | 10/2009 |
| WO | 2009/123560 A1 | 10/2009 |
| WO | 2009/126106 A1 | 10/2009 |
| WO | 2009/153225 A1 | 12/2009 |
| WO | 2010/003860 A2 | 1/2010 |
| WO | 2010/015726 A1 | 2/2010 |
| WO | 2010015726 A1 | 2/2010 |
| WO | 2010/092239 A1 | 8/2010 |
| WO | 2010092239 A1 | 8/2010 |
| WO | 2010/102802 A1 | 9/2010 |
| WO | 2010112519 | 10/2010 |
| WO | 2010115785 | 10/2010 |
| WO | 2010/125247 A2 | 11/2010 |
| WO | 2010/131016 A2 | 11/2010 |
| WO | 2010131016 A2 | 11/2010 |
| WO | 2011/004300 A1 | 1/2011 |
| WO | 2011/004301 A1 | 1/2011 |
| WO | 2011/042607 A1 | 4/2011 |
| WO | 2011/048000 al | 4/2011 |
| WO | 2011/056130 A1 | 5/2011 |
| WO | 2011/059398 A1 | 5/2011 |
| WO | 2011/064441 A1 | 6/2011 |
| WO | 2011/068457 A1 | 6/2011 |
| WO | 2011/134938 A2 | 11/2011 |
| WO | 2011/134939 A1 | 11/2011 |
| WO | 2011/141876 A1 | 11/2011 |
| WO | 2011/141877 A1 | 11/2011 |
| WO | 2011134938 A1 | 11/2011 |
| WO | 2011134939 A1 | 11/2011 |
| WO | 2011/154335 A1 | 12/2011 |
| WO | 2012/039668 A1 | 3/2012 |
| WO | 2012/098296 A2 | 7/2012 |
| WO | 2014/091212 A1 | 6/2014 |

OTHER PUBLICATIONS

Written Opinion of the International Searching Authority for PCT Application No. PCT/EP2011/056540.
Third Party Observation dated Jan. 9, 2012 for European Application No. 10161173.9.
Third Party Observation dated Jun. 11, 2012 for European Application No. 10161173.9.
Third Party Observation dated Apr. 19, 2013 for European Application No. 10161173.9.
The Office Action dated Sep. 24, 2012 for European Application No. 10711 423.3-2115.
The Office Action dated Jan. 16, 2013 for Chinese Application No. 201080015262.5.
Third Party Observations dated May 27, 2011 for European Application No. 09156683.6.
The European Search Report dated Jun. 26, 2009 for European Application No. EP 09156683.6.
Siró et al. "Microfibrillated cellulose and new nanocomposite materials: A Review." Cellulose (2010): 17, pp. 459-494.
Falini et al. "Oriented Crystallization of Vaterite in Collagenous Matrices," Chem. Eur. J., 1998, 4, 1048-1052.
Campinhos, Jr. "Sustainable plantations of high-yield Eucalyptus trees for production of fiber: the Aracruz case," New Forests, 1999, 17, 129-143.
Auad et al. "Characterization of nanocellulose-reinforced shape memory polyurethanes," Polymer International, 2008, 57, 651-659. Online Publication Date: Dec. 13, 2007.
Kenny et al. "Lime and Limestone," Ullmann's Encyclopedia of Industrial Chemistry, 2012, vol. 21, 37-69.
Dupont, "Cellulose in lithium chloride/N,N-dimethylacetamide, optimisation of a disslution method using paper substrates and stability of the solutions," Polymer, 2003, 44, 4117-4126.
Patt et al. "Paper and Pulp," Ullmann's Encyclopedia of Industrial Chemistry, Published online: Jun. 2000.
The 3rd Party Observations dated Jun. 11, 2012 for related European Patent Application No. 10161166.3.
The Communication from the European Patent Office dated Aug. 6, 2013 for European Patent Application No. 11716257.8.
The Response to the Communication dated Nov. 5, 2013 for European Patent Application No. 11716257.8.
Shen et al. "Carbohydrate-based fillers and pigments for papermaking: A Review," 2011, Carbohydrate Polymers, vol. 85, 17-22.
Chauhan et al. "Use of Nanotechnology for High Performace Cellulosic and Papermaking Products," 2012, Cellulose Chemistry and Technology, 46 (5-6), pp. 389-400.
Charrani et.al., "Rheological characterization of high concentrated MFC gel from kenaf unbleached pulp," 2013, Cellulose, vol. 20, pp. 727-740.
Opietnik et al., "TENCHEL® Gel—A novel Cellulose Micro Suspension," 2013, Lenzinger Berichte, vol. 91, pp. 89-92.
The International Search Report for PCT Application No. PCT/EP2011/056540.
The Written Opinion of the International Searching Authority for PCT Application No. PCT/EP2011/056540.
The Office Action dated Jan. 27, 2014 for U.S. Appl. No. 13/138,646.
The Office Action dated Jan. 28, 2014 for U.S. Appl. No. 13/138,647.
Third Party Observations dated Jun. 6, 2012 for EP 09156703.2.
Third Party Observations dated Oct. 21, 2011 for EP 09156703.2.
European Search Report dated Jun. 26, 2009 for EP 09156703.2.
Third Party Observations dated Apr. 12, 2013 for EP 10161166.3.
Third Party Observations dated Jun. 11, 2012 for EP 10161166.3.
Third Party Observations dated Jan. 9, 2012 for EP 10161166.3.
Third Party Observations dated Feb. 4, 2013 for EP 11716257.8.
Third Party Observations dated Feb. 4, 2013 for EP 11719499.3.
Third Party Observations dated Jun. 6, 2012 for EP 09156683.6.
Third Party Observations dated Oct. 21, 2011 for EP 09156683.6.
Third Party Observations dated Jun. 11, 2012 for EP 10713884.4.
Third Party Observations dated Feb. 17, 2012 for EP 10713884.4.
Third Party Observations dated Jun. 11, 2012 for EP 10711423.3.
Third Party Observations dated Feb. 17, 2012 for EP 10711423.3.
Third Party Observations dated May 18, 2011 for EP 09156703.2.
Subramanian et al. "Calcium carbonate—cellulose fibre composites; the role of pulp refining." Paper Technology, Dec. 2006, pp. 1 to 5.
Subramanian "Engineering fine paper by utilising the structural elements of the raw materials." Helsinki University of Technology, Department of Forest Products Technology, Series A1, Espoo 2008, pp. 1 to 66.
Australia, Patent Examination Report No. 1 dated May 14, 2013 from corresponding Australian Patent Application No. 2011246521 filed on Apr. 26, 2011.

(56) References Cited

OTHER PUBLICATIONS

Canada, Examination Report dated Sep. 2, 2015 from corresponding Canadian Patent Application No. 2,796,132 filed on Apr. 26, 2011.
Canada, Examination Report dated Apr. 28, 2016 from corresponding Canadian Patent Application No. 2,796,132 filed on Apr. 28, 2011.
China, First Office Action dated May 6, 2014 from corresponding Chinese Patent Application No. 201180020949.2 filed on Apr. 26, 2011.
China, Second Office Action dated Mar. 4, 2015 from corresponding Chinese Patent Application No. 201180020949.2 filed on Apr. 26, 2011.
Columbia, Office Action dated Sep. 3, 2013 from corresponding Columbian Patent Application No. 12-182.195 filed on Apr. 26, 2011.
Europe, First Office Action dated Oct. 11, 2013 from corresponding European Patent Application No. 11 719 499.3 filed on Apr. 26, 2011.
Europe, Second Office Action dated Mar. 29, 2016 from corresponding European Patent Application No. 11 719 4993 filed on Apr. 26, 2011.
Japan, Notice of Rejection dated Apr. 31, 2015 from corresponding Japanese Patent Application No. 2013-506620 filed on Apr. 26, 2011.
Japan, Official Action dated Oct. 27, 2015 from corresponding Japanese Patent Application No. 2013-506620 filed on Apr. 26, 2011.
Korea, Office Action dated Jul. 29, 2016 from corresponding Korean Patent Application No. 10-2012-7030744 filed on Apr. 26, 2011.
Malaysia, Examination Report dated Oct. 15, 2015 from corresponding Malaysian Patent Application No. PI 2012004747 filed on Apr. 26, 2011.
Vietnam, First Examination Report dated Dec. 30, 2014 from corresponding Vietnamese Patent Application No. 1-2012-03429 filed on Apr. 26, 2011.
Vietnam, Second Examination Report dated Oct. 8, 2015 from corresponding Vietnamese Patent Application No. 1-2012-03429 filed on Apr. 26, 2011.
Vietnam, Third Examination Report dated Apr. 28, 2016 from corresponding Vietnamese Patent Application No. 1-2012-03429 filed on Apr. 26, 2011.
U.S. Non-Final Office Action dated Jan. 22, 2013 for U.S. Appl. No. 13/138,647, 19 pages.
U.S. Non-Final Office Action dated Sep. 11, 2013 for U.S. Appl. No. 13/138,646, 13 pages.
U.S. Non-Final Office Action dated Sep. 11, 2013 for U.S. Appl. No. 13/138,647, 17 pages.
U.S. Notice of Allowance dated Feb. 23, 2018 for U.S. Appl. No. 14/474,749, 9 pages.
U.S. Notice of Allowance dated May 23, 2014 for U.S. Appl. No. 13/138,647, 8 pages.
U.S. Notice of Allowance dated May 27, 2014 for U.S. Appl. No. 13/138,646, 8 pages.
U.S. Notice of Allowance dated Sep. 16, 2014 for U.S. Appl. No. 13/138,646, 7 pages.
U.S. Notice of Allowance dated Sep. 5, 2014 for U.S. Appl. No. 13/138,647, 7 pages.
U.S. Non-Final Office Action dated Mar. 19, 2018 for U.S. Appl. No. 14/474,705 ,8 pages.
U.S. Notice of Allowance dated Dec. 22, 2017 for U.S. Appl. No. 14/808,480, 8 pages.
U.S. Non-Final Office Action dated May 19, 2017 for U.S. Appl. No. 14/808,480, 6 pages.
U.S. Final Office Action dated Nov. 28, 2016 for U.S. Appl. No. 14/808,480, 8 pages.
U.S. Non-Final Office Action dated May 2, 2016 for U.S. Appl. No. 14/808,480, 15 pages.
U.S. Non-Final Office Action dated Oct. 21, 2015 for U.S. Appl. No. 14/808,480, 11 pages.
U.S. Notice of Allowance dated Dec. 21, 2017 for U.S. Appl. No. 13/640,533, 7 pages.
U.S. Non-Final Office Action dated Sep. 1, 2017 for U.S. Appl. No. 13/640,533, 8 pages.
U.S. Notice of Allowance dated May 22, 2017 for U.S. Appl. No. 13/640,533, 6 pages.
U.S. Final Office Action dated Nov. 28, 2016 for U.S. Appl. No. 13/640,533, 8 pages.
U.S. Non-Final Office Action dated Mar. 24, 2016 for U.S. Appl. No. 13/640,533, 12 pages.
U.S. Notice of Allowance dated Nov. 25, 2015 for U.S. Appl. No. 13/640,533, 8 pages.
U.S. Notice of Allowance dated Aug. 20, 2015 for U.S. Appl. No. 13/640,533, 6 pages.
U.S. Notice of Allowance dated Jan. 20, 2015 for U.S. Appl. No. 13/640,533, 5 pages.
U.S. Notice of Allowance dated Dec. 2, 2014 for U.S. Appl. No. 13/640,533, 8 pages.
U.S. Non-Final Office Action dated Apr. 25, 2014 for U.S. Appl. No. 13/640,533, 15 pages.
U.S. Final Office Action dated Dec. 19, 2014 for U.S. Appl. No. 13/640,533, 8 pages.
U.S. Non-Final Office Action dated Jun. 14, 2013 for U.S. Appl. No. 13/640,533, 15 pages.
UK Search Report for UK Application No. GB0908401.3, dated Sep. 14, 2009, 1 page.
Ukraine, Office Action for Ukrainian Application No. a2011 12682.
Waterhouse, J .F., "Whither Refining?", Institute of Paper Science and Technology, No. 649, 1997, 40 pages.
Yano, Hiroyuki, "High Performance of Bio Fibers by the Addition of Filler", vol. 55, Machine No. 4, 2009, pp. 63-68.
Zhao, et al., "Ultrasonic technique for extracting nanofibers from nature materials" Applied Physics Letters 90, 073112, 2007, 2 pages.
Zirconium Oxide Data sheet, downloaded online from www.stanfordmaterials.com, downloaded on Jan. 12, 2012, 7 pages.
Zirconium, Silicate Data sheet, downloaded online from www.reade.com, downloaded on Jan. 12, 2012, 2 pages.
Zou, et al. "Production of Nanocrystalline Cellulose and its Potential Applications in Specialty Papers." Pira Specialty Papers Conference, Nov. 2010, pp. 1-30.
Zou, et al. "Review of Microfibrillated Cellulose (MFG) for Papermaking", Pulp and Paper Engineering, School of Chemical and Biomolecular Eng., Georgia Institute of Technology, 10 pages.
U.S. Notice of Allowance dated May 11, 2018 for U.S. Appl. No. 13/640,533, 7 pages.
U.S. Notice of Allowance dated Apr. 24, 2018 for U.S. Appl. No. 14/808,480, 8 pages.
"Paper Coating Pigments," TAPPI Monograph Series No. 30, 1966, pp. 34-35.
Abe, et al. "Obtaining Cellulose Nanofibers with a Uniform Width of 15 nm from Wood", Bio macromolecules, vol. 8, 2007, pp. 3276-3278.
Ahola et al., "Model Films from Native Cellulose Nanofibrils. Preparation, Swelling, and Surface Interactions," Biomacromolecules, 9: 2008 pp. 1273-1282.
Ahola, Susanna, "Properties and Interfacial Behavior of Cellulose Nano fibrils." Doctoral Thesis, 2008, 82 pages.
Ankerfors, et al. "Nano Cellulose Developments in Scandinavia", Paper and Coating Chemistry Symposium (PCCS), Jun. 2009, Hamilton, Canadian, 43 pages.
Ankerfors, Mikael, "The manufacture of micro fibrillated cellulose (MFC) its applications." Nanostructured cellulose and new cellulose derivatives seminar, Nov. 2006, pp. 1-40.
ATREX G-Series, Megatrex, "Technology for Reject Treatment and Recovery." 2 pages.
Australian Examination Report dated May 3, 2013 for Australian Patent Application No. 2011246522, 4 pages.
Australian Patent Examination Report No. 1 dated Feb. 26, 2014 for Australian Patent Application No. 2013202515, 3 pages.

(56) References Cited

OTHER PUBLICATIONS

Australian Patent Examination Report dated Jul. 26, 2012 for Australian Patent ApplicationNo. 2010247184, 6 pages.
Australian Patent Examination Report No. 1, dated Sep. 16, 2015 for Australian Patent Application No. 2014227494, 3 pages.
Berglund et al., "Nanostructured Cellulose Products." Finnish-Swedish Wood Material Science Research Programme Opening Seminar, 2004, Helsinki, Finland, 28 pages.
Bhatnagar et al., "Processing of Cellulose Nanofiber-reinforced Composites." Journal of Reinforced Plastics and Composites, vol. 24, No. 12, 2005, pp. 1259-1268.
Canadian Office Action dated Apr. 26, 2016 for Canadian Patent Application No. 2, 796, 135, 4 pages.
Canadian Office Action dated May 11, 2015 for Canadian Patent Application No. 2,755,495, 4 pages.
Canadian Office Action dated Sep. 3, 2015 for Canadian Patent Application No. 2, 796, 135, 3 pages.
Canadian Office Action for Canadian Patent Application No. 2755493, dated Feb. 19, 2015, 3 pages.
Canadian Office Action for Canadian Patent Application No. 2755493, dated May 28, 2014, 4 pages.
Canadian Office Action dated Dec. 18, 2013 for Canadian Application No. 2,748,137, 2 pages.
Canadian Office Action dated Jan. 7, 2014 for Canadian Application No. 2,755,495, 2 pages.
Characterisation Newsletter "Micro fibrillated Cellulose", No. 5, Jan. 2009, pp. 1-2.
Chinese Fifth Office Action dated Feb. 15, 2016 for Chinese Patent Application No. 201080015263.X, 7 pages.
Chinese First Notification of Office Action for Chinese Patent Application No. 201510628033.5, dated Jan. 10, 2017, 17 pages.
Chinese Fourth Office Action dated Oct. 13, 2015 for Chinese Patent Application No. 201080015263.X, 10 pages.
Chinese Office Action dated Apr. 10, 2015 for Chinese Patent Application No. 201180020953.9, 5 pages.
Chinese Office Action dated Jan. 13, 2015 for Chinese Patent Application No. 201180020953.9, 12 pages.
Chinese Office Action dated May 22, 2014 for Chinese Patent Application No. 201180020953.9, 20 pages.
Chinese Office Action for Chinese Patent Application No. 201080015262.5 dated Jul. 9, 2013, 6 pages.
Chinese Office Action for Chinese Patent Application No. 201610882363.1, dated Jan. 25, 2018, 27 pages.
Chinese Office Action dated Jan. 6, 2014 for Chinese Application No. 201080003690.6, 15 pages.
Chinese Second Office Action dated Jun. 11, 2014 for Chinese Patent Application No. 201080015263.X, 14 pages.
Chinese Third Office Action dated Feb. 27, 2015 for Chinese Patent Application No. 201080015263.X, 23 pages.
Chinese, First Office Action dated Oct. 23, 2013 from Chinese Patent Application No. 201080015263.X.
Chinese, Office Action dated Jan. 16, 2013 for Chinese Application No. 201080015262.5, 11 pages.
Chinga-Carrasco and Syverud, "Computer-Assisted Quantification of the Muli-Scale Structure of Films Made of Nanofibrillated Cellulose," J Nanopart Res (2010) 12:841-851.
Chinga-Carrasco, "Cellulose fibres, nanofibrils and microfibrils: The morphological sequence of MFC components from a plant physiology and fibre technology point of view." Chinga-Carrasco Nanoscale Research Letters 2011, vol. 6:417, 8 pages.
Crofton et al., " Dielectric Studies of Cellulose and Its Derivatives: 1. Acetylation of Cellulose," Polymer (1982) 23:1605-1608.
De Oliveira et al., "Synthesis and Characterization of Microcrystalline Cellulose Produced from Bacterial Cellulose," J. Therm. Anal. Caiorim, (2011) 106, pp. 703-709.
Decision Revoking European Patent No. 2236664 dated Nov. 2, 2017, 12 pages.
Ducheyne, Paul et al., eds "Comprehensive Biomaterials," vol. 1. Newnes, 2015, p. 409.

Eichhorn et al., "Review: current international research into cellulose nanofibres and nanocomposites." Journal of Materials Science, vol. 45, No. 1, 2010, pp. 1-33.
Eriksen et al., "The use of microfibrillated cellulose produced from kraft pulp as strength enhancer in TMP paper." Nordic Pulp and Paper Research Journal, vol. 23. No. 3, 2008, p. 299-304.
Esau, Katherine, "Chapter 4, Cell Wall," Anatomy of Seed Plants, 2nd Edition, (1977) pp. 43-48.
European Examination Report dated Oct. 27, 2015 for European Patent Application No. 14 175 471.3, 3 pages.
European Examination Report dated Oct. 27, 2015 for European Patent Application No. 14 175 451.5, 3 pages.
European Examination Report dated Sep. 16, 2016 for European Patent Application No. 14 175 471.3, 4 pages.
European Extended European Search Report dated Jan. 15, 2013, for European Patent Application No. 12189681.5, 5 pages.
European Extended Search Report for European Patent Application No. 14175471.3 dated Oct. 23, 2014, 8 pages.
European Notice of Opposition dated Dec. 19, 2014 for European Patent No. EP2386682, 17 pages.
European Notice of Opposition dated Dec. 19, 2014 for European Patent No. EP2386683, 15 pages.
Silenius, Petri, "Improving the Combinations of Critical Properties and Process Parameters of Printing and Writing Papers and Paperboards by New Paper-Filling Methods", Helsinki University of Technology Laboratory of Paper Technology Reports, Series A 14, Espoo 2002, 168 pages.
Sinnott et al., "Slurry Flow in a Tower Mill," Seventh International Conference on CFO in the Minerals and Process Industries, CSIRO, Melbourne, Austrialian, Dec. 9-11, 2009, pp. 1-7.
Siqueira et al., "Cellulosic Bionanocomposites: A Review of Preparation, Properties and Applications," Polymers (2010) 2, pp. 728-765, doi: 10.3390/polym2040728.
Sixta "Handbook of Pulp." Wood Structure and Morphology (2006), vol. 1, 41-42.
Smook, Handbook for Pulp and Paper Technologies, 1992, Angus Wilde Publications, 2nd Edition, Chap. 13.
Sofia et al., "A Comparison of Cellulose Nanocrystals and Cellulose Nanofibers Extracted from Bagasse Using Acid and Ball Milling Methods," Adv. Nat Sci.: Nanosci. Nanotechnol., (2016) 7, 9 pages.
Somboon, et al. "Grit segments in TMP refining. Part 1: Operating parameters and pulp quality", Appita Journal, vol. 62 No. 1, 2009, pp. 37-41.
Somboon, et al. Grit segments in TMP refining. Part 2: Potential for energy reduction, Appita Journal, vol. 62, No. 1, 2009, pp. 42-45 and 59.
Somboon, Phichit, "On the Application of Grits to Therrnomechanical Pulp Refining." TKK Reports in Forest Products Technology, Series A7, Espoo 2009, 61 pages.
Spence, et al. "The effect of chemical composition on microfibrillar cellulose films from wood pulps: Mechanical processing and and physical properties", BioResource Technology, vol. 101, 2010, pp. 5961-5968.
Statement of Grounds of Appeal for European Patent No. 2236664 dated Mar. 12, 2018, 13 pages.
Subramanian et al., "Calcium Carbonate—Cellulose Fibre Composites; the Role of Pulp Refining," Paper Technology, Dec. 2006 Pulp Refining, pp. 27-31.
Summons to Attend Oral Proceedings Pursuant to Rule 115(1) EPC dated Mar. 22, 2017 for corresponding European Patent No. EP2236664, 10 pages.
Syverud and Stenius, "Strength and Barrier Properties of MFC Films," Cellulose 16:75-85 (2009).
Syverud, et al. "The influence of microfibrillated cellulose, MFG, on paper strength and surface properties", pp. 1-32.
Taiwan Examination and Search Report dated Apr. 29, 2016 for Taiwan Patent Application No. 100114616, 11 pages.
Taiwan Examination and Search Report dated May 17, 2016 for Taiwan Patent Application No. 100114616, 11 pages.
Taiwan Examination Report and Search Report for Taiwan Patent Application No. 099109560 dated Jun. 22, 2015, 12 pages.
Taiwan Examination Report dated Feb. 11, 2014 for Taiwanese Application No. 099109562, 17 pages.

(56) References Cited

OTHER PUBLICATIONS

Taiwan Reasons for Rejection dated Apr. 26, 2017 for Taiwanese Application No. 099109562, 5 pages.
Taiwan, Office Action for related Taiwanese Application No. 099115704, dated Jul. 14, 2014.
Taiwan Reasons for Rejection dated Nov. 7, 2014 for Taiwanese Application No. 099109562, 7 pages.
Taiwan Office Action for Taiwanese Application No. 1-2012-03429, dated Dec. 30, 2014, 4 pages.
Taiwan Office Action for Taiwanese Application No. 1-2012-03429, dated Oct. 8, 2015, 3 pages.
Taiwan Office Action for Taiwanese Application No. 1-2012-03429, dated Apr. 28, 2016, 2 pages.
Taiwanese Office Action and Search Report for Taiwanese Patent Application No. 104124236 dated Feb. 26, 2018, 10 pages.
Taniguchi, Takashi, "New Films Produced from Microfibrillated Natural Fibres", Polymer International, vol. 47, 1998, pp. 291-294.
Terao, et al. "Pulp-Filler Interaction (3)—The Influence of Wet Pressing and Cellulosic Fines Addition on the Structure and Properties of Filler Loaded Papers", vol. 8, 1989, pp. 65-73.
Third Party Observations dated Mar. 16, 2015 for European Patent Application No. 14 175 451.5, 6 pages.
Third Party Observations dated Mar. 16, 2015 for European Patent Application No. 14175471.3, 6 pages.
Third Party Written Submission dated Sep. 25, 2017 for corresponding European Patent No. 2236664, 2 pages.
Torvinen, et al. "Flexible filler—nanocellulose structures", VTT Technical Research Centre of Finland—1 page.
Turbak, A. F., "Birth of Nanocellulose," online publication from TAPPI, http://www.naylornetwork.com/PPI-OTW/articles/print.asp?aid=150993, retrieved Nov. 1, 2015.
U.S. Final Office Action dated Aug. 4, 2017 for U.S. Appl. No. 14/474,705, 14 pages.
U.S. Final Office Action dated Jan. 27, 2014 for U.S. Appl. No. 13/138,646, 14 pages.
U.S. Final Office Action dated Jan. 28, 2014 for U.S. Appl. No. 13/138,647, 18 pages.
U.S. Final Office Action dated Jul. 20, 2017 for U.S. Appl. No. 14/474,749, 12 pages.
U.S. Final Office Action dated May 6, 2016 for U.S. Appl. No. 14/474,705, 11 pages.
U.S. Final Office Action dated May 8, 2013 for U.S. Appl. No. 13/138,646, 11 pages.
U.S. Final Office Action dated May 9, 2013 for U.S. Appl. No. 13/138,647, 15 pages.
U.S. Final Office Action dated May 9, 2016 for U.S. Appl. No. 14/474,749, 10 pages.
U.S. Issue Fee Payment dated Sep. 11, 2014 for U.S. Appl. No. 13/138,647, 5 pages.
U.S. Issue Fee Payment dated Sep. 17, 2014 for U.S. Appl. No. 13/138,646, 5 pages.
U.S. Issue Notification dated Oct. 28, 2014 for U.S. Appl. No. 13/138,647, 1 page.
U.S. Issue Notification dated Oct. 8, 2014 for U.S. Appl. No. 13/138,646, 1 page.
U.S. Non-Final Office Action dated Dec. 19, 2016 for U.S. Appl. No. 14/474,749, 12 pages.
U.S. Non-Final Office Action dated Dec. 3, 2015 for U.S. Appl. No. 14/474,705, 13 pages.
U.S. Non-Final Office Action dated Dec. 3, 2015 for U.S. Appl. No. 14/474,749, 11 pages.
U.S. Non-Final Office Action dated Feb. 10, 2017 for U.S. Appl. No. 14/474,705, 15 pages.
U.S. Non-Final Office Action dated Jan. 15, 2013 for U.S. Appl. No. 13/138,646, 16 pages.
Korean Office Action for Korean Patent Application No. 10-2017-7011268 dated Jun. 21, 2017, 5 pages.
Kumar et al. "Comparison of nano-and micro fibrillated cellulose films." Cellulose (2014) 21: 3443-3456.

Lavoine et al., "Microfibrillated Cellulose—Its Barrier Properties and Applications in Cellulosic Materials: A Review," Carbohydrate Polymers 90 (2012) pp. 735-764.
Little et al. "Hydrated lime—more than just a filler." National Line Association. May 2001 p. 1-15.
Littunen, Kuisma, "Free radical graft copolymerization of microfibrillated cellulose", Master's Thesis, Helsinki University of Technology, Sep. 2009, 83 pages.
Luukkanen, Lauri, "Reducing of Paper Porosity and Roughness Through Layered Structure", Aalto University School of Science and Technology, Master's thesis for the degree of Master of Science in Technology, Espoo, May, 2010, 132 pages.
Malaysian Examination Report dated Nov. 30, 2015 for Malaysian Patent Application No. PI 2011004631, 3 pages.
Malaysian Substantive Examination Report for Malaysian Patent Application No. PI 2014002508 dated Nov. 30, 2017, 4 pages.
Mathur V. "GRI's Fibrous Filler Technology Presentation to TAPPI", Philadelphia, PA (slides only), 2005, pp. 1-10.
McGinnis and Shafizadeh, "Chapter 1 Cellulose and Hemicellulose," Pulp and Paper: Chemistry and Chemical Technology, (1980) pp. 1-38.
McGraw-Hill, "Cell Walls (Plant)," Encyclopedia of Science and Technology, 5th edition, (1982), pp. 737-741.
Mill (grinding) http://en_wikipedia.org/w/index.php?title-File:Hammer_mill_open-_front_full.jgp, 8 pgs.
Mori, et al. "Effect of cellulose nano-fiber on calcium carbonate crystal form", Polymer Preprints, Japanese vol. 56, No. 2007—1 page.
Morseburg, et al. "Assessing the combined benefits of clay and nanofibrillated cellulose in layered TMP-based sheets", Cellulose, No. 5, vol. 16, 2009, pp. 795-806.
Mullite, 2001 [downloaded online Dec. 6, 2016], Minerals Data Publishing.
Nakagaito, et al. "The effect of fiber content on the mechanical and thermal expansion properties of bio composites based on microfibrillated cellulose", Cellulose, vol. 15, 2008, pp. 459-494.
New Zealand Office Action for New Zealand Patent Application No. 603756 dated Jun. 20, 2013, 2 pages.
Notice of Appeal filed Dec. 21, 2017 for corresponding European Patent No. EP2236664, 1 page.
Notice of Opposition against EP 2236664 B1, EP Application No. 09156683.6, dated Jul. 18, 2017 from European Patent Office, 10 pages.
Notice of Opposition against EP 2236664 B1, EP Application No. 09156683.6, dated Sep. 29, 2016 from European Patent Office, 1 page.
Notice of Opposition dated Dec. 19, 2014 for European Patent No. EP238682, 22 pages.
Notice of Opposition to European Patent No. 2236545 dated May 27, 2015, 19 pages.
OPTIFINER™ DF Deflakers, "Improved quality through effective deflaking." Stock Preparation and Recycled Fiber Systems, Metso Paper, 4 pages, 2006.
Paakko et al., ""Enzymatic Hydrolysis Combined with Mechanical Shearing and High-Pressure Homogenization for Nanoscale Cellulose Fibrils and Strong Gels."" Biomacromolecules (2007) 8, 1934-1941.
Peltola, Maarit, "Preparation of Microfibrillated Cellulose" Master of Science Thesis, Tampere University of Technology, May 2009, 98 pages.
Peng et al., "Drying cellulose nanofibrils: in search of a suitable method." Published online: Dec. 2, 2011, Cellulose, DOI 10.1007/s10570-011-9630-z, 12 pages.
Pinkney et al., "Microfibrillated Cellulose—A New Structural Material." Engineering Doctorate Conference (2012), Unviersity of Birminghamm 2 pages.
Pöhler, Tiina & Lappalainen, Timo & Tammelin, Tekla & Eronen, Paula & Hiekkataipale, Panu & Vehniäinen, Annikki M. Koskinen, Timo. (2011). "Influence of fibrillation method on the character of nanofibrillated cellulose (NFC)," 2010 TAPPI International Conference on Nanotechnology for the Forest Product Industry, Dipoli Congress Centre, Espoo, Finland, Sep. 27-29, 2010, 22 pages.

(56) References Cited

OTHER PUBLICATIONS

Porubska, et al. "Homo- and heteroflocculation of papermaking fines and fillers", Colloids and Surfaces A: Physiochem. Eng. Aspects, Elsevier Science, vol. 210, 2002, pp. 223-230.
Postek et al., "Production and Applications of Cellulose Nanomaterials," TAPPI Press (2013) Chapter 2, pp. 169-173.
Product information for the Ultra-fine Friction Grinder "Supermasscolloider," 1 page, retrieved from http:www.masuko.com/English/product/Masscolloder.html (2014).
Provision of the minutes in accordance with Rule 124(4) EPC dated Nov. 2, 2017, of the oral proceedings for corresponding European Patent No. EP2236664, 5 pages.
Ragnar et al., "Pulp," Ullmann's Encyclopedia of Industrial Chemistry, published on-line 2000, 89 pages.
Response dated Mar. 2, 2017 to Communication of Notices of Opposition Pursuant Rule 79(1) EPC for corresponding European Patent No. 2236664, 9 pages.
Response to Notice of Opposition Against EP2236664, dated Mar. 2, 2017, submitted to the European Patent Office, 9 pages.
Roberts, J.C., "Chapter 2, The Material of Paper," The Chemistry of Paper, RSC Paperbacks, 1996, pp. 11-25.
Roberts, J.C., "Chapter 4, The Material of Paper," The Chemistry of Paper, RSC Paperbacks, 1996, pp. 52-68.
Rowland and Roberts, "The Nature of Accessible Surfaces in the Microstructure of Cotton Cellulose," Journal of Polymer Science: Part A-1, vol. 10, (1972) pp. 2447-2461.
Russian Office Action dated Mar. 30, 2010 for Russian Application No. 2011143811.
Russian Office Action from Russian Patent Application No. 2011143854 filed on Mar. 10, 2010.
Russian Official Action dated Apr. 22, 2015 from Russian Patent Application No. 2015109771.
Russian Office Action dated Jan. 21, 2014 for Russian Patent Application No. 2011143854, 7 pages.
Russian Official Action dated Apr. 22, 2015 for Russian Patent Application No. 2015109771, 4 pages.
Russian Office Action dated Apr. 22, 2015 for Russian Patent Application No. 2012150441, 7 pages.
Saito et al., "Cellulose Nanofibers Prepared by TEMPO-Mediated Oxidation of Native Cellulose," Biomacromolecules, 8:2485-2491. (2007).
Saito, et al. Homogeneous Suspensions of Individualized Microfibrils from TEMPO-Catalyzed Oxidation of Native Cellulose Biomacromolecules, American Chemical Society, vol. 7, No. 6, 2006, pp. 1687-1691.
Samir et al., "Review of Recent Research into Cellulosic Whiskers, Their Properties and Their Application in Nanocomposite Field," Biomacromolecules (2005) 6, pp. 612-626.
Selder, H.; Mannes, W., and Matzke, W., "Broke systems for LWC, MWC and HWC Papers", Voith Sulzer Paper Technology, 8 pages, Dec. 2011.
Singapore Office Action for Singapore Patent Application No. 2012075610, dated Dec. 31, 2014, 21 pages.
Singapore Search and Examination Report for Singapore Patent Application No. 2012075610, dated Nov. 4, 2015, 16 pages.
European Office Action dated Jun. 27, 2011 for European Application No. 09156683.6, 7 pages.
European Office Action dated Sep. 20, 2016 for European Patent Application No. 14 175 451.5, 3 pages.
European Office Action for corresponding European Patent Application No. 14175471.3 dated Oct. 6, 2017, 3 pages.
European Office Action from the European Patent Office dated Mar. 15, 2013 for European Patent Application No. 10 161 166.3, 4 pages.
European Office Action dated Feb. 6, 2014 for related European Application No. 12 189 681.5-1308, 3 pages.
European Office Action dated Mar. 7, 2014, for European Application No. 10 727 476.3-1308, 5 pages.
European Office Action dated May 26, 2014, for European Application No. 10 727 476.3-1308, 4 pages.
European Office Action dated Nov. 30, 2012 for European Application No. 10 727 476.3-2124, 4 pages.
European Office Action dated Oct. 25, 2013 for European Application No. 10 727 476.3-1308, 3 pages.
European Office Action dated Mar. 10, 2017 for European Patent Application No. 10 713 884.4, 4 pages.
European Partial European Search Report of European Application No. 16163032, dated Jul. 26, 2016, 3 pages.
European Search Report dated Oct. 23, 2014 for European Patent Application No. 14 175 451.5, 6 pages.
European Search Report dated Sep. 8, 2010 for European Application No. 10161166.3, 6 pages.
European Search Report for European Patent Application No. 17188196.4, dated Nov. 17, 2017, 6 pages.
European Third Party Observations dated Apr. 12, 2013 for European Application No. EP 10161173.9, 4 pages.
European Third Party Observations dated May 18, 2011 for European Application No. 09156683.6, 6 pages.
European Third Party Observations pursuant to Article 115(1 )EPC concerning European Patent Application No. 12 189 681.5, dated Jul. 10, 2014, 15 pages.
European Third Party Observations pursuant to Article 115(1)EPC concerning European Patent Application No. 10727476.3, dated Jul. 22, 2014, 18 pages.
European Communication from the European Patent Office dated Aug. 6, 2013 for European Patent Application No. 11716257.8.
European Search Report dated Sep. 7, 2010 for European Application No. 10161173.9, 6 pages.
European Examination Report dated May 2, 2016 from European Patent Application No. 10 713 884.4.
European Office Action dated Feb. 15, 2013 for European Application No. 11716257.8, 2 pages.
European Office Action dated Feb. 21, 2013 for European Application No. 10713884.4, 4 pages.
European Office Action dated Feb. 7, 2013 for European Application No. 09156683.6, 3 pages.
European Office Action dated Feb. 7, 2013 for European Application No. 09156703.2, 3 pages.
European Office Action dated Jan. 2, 2014 for European Application No. 09156683.6, 3 pages.
European Office Action dated Jan. 2, 2014 for European Application No. 10713884.4, 2 pages.
European Office Action dated Jul. 31, 2013 for European Application No. 09156683.6, 3 pages.
European Office Action dated Jul. 31, 2013 for European Application No. 09156703.2, 3 pages.
European Office Action dated Mar. 15, 2013 for European Application No. 10161173.9.
European Office Action dated Mar. 26, 2014 for European Application No. 10711423.3, 6 pages.
European Office Action dated May 20, 2011 for European Application No. 09156703.2, 4 pages.
European Office Action dated Oct. 11, 2013 for European Application No. 11719499, 4 pages.
European Search Report for European Patent Application No. 18152927.2, dated May 7, 2018, 6 pages.
European Search Search Report dated Jun. 26, 2009 for European Application No. EP 09156683.6, 9 pages.
European Search Report for European Patent Application No. 17190151.5, dated Mar. 19, 2018, 5 pages.
European Office Action for European Patent Application No. 10713884.4, dated Apr. 19, 2018, 4 pages.
European Third Party Observation dated Jan. 9, 2012 for European Application No. 10161173.9, 6 pages.
European Examination Report from the European Patent Office dated Mar. 15, 2013 from European Patent Application No. 10 161 166.3, 4 pages.
Fahn, A., "Plant Anatomy Fourth Edition," (1990) pp. 32-39.
Fengel et al., "Chapter 4. Cellulose," Wood Chemistry, Ultrastructure, Reactions, (1983) pp. 66-105.
Fengel, D., "Ideas on the Ultrastructure Organization of the Cell Wall Components," J. Polymer Sci.: Part C, No. 36 pp. 383-392. (1971).

(56) References Cited

OTHER PUBLICATIONS

Frey-Wyssling and Mühlethaler, "The Fine Structure of Cellulose." Fortschritte der Chemie Organischer Naturstoffe (1951) pp. 1-27.
Fukui, Yoshitaka, "Microfibrillated Cellulose", vol. 60, No. 24, 1985, pp. 5-12.
GL&V, The Atrex System at M-real Hallein Paper Mill in Austria, "Atrex is running well and us money!" 4 pages.
Habibi et al., "Cellulose Nanocrystals: Chemistry, Self-Assembly, and Applications," Chem. Rev. (2010) 110, pp. 3479-3500.
Hamann, Lutzm Papiertechnische Stiftung, SUNPAP Workshop May 10, 2011, Seventh Framework Programme, 24 pages.
Henriksson, "Cellulose Nanofibril Networks and Composites", KTH Chemical Science and Engineering, 2008, 60 pages.
Henriksson, et al. "Cellulose Nanopaper Structures of High Toughness", Biomacromolecules, vol. 9, 2008, pp. 1579-1585.
Hentze, Hans-Peter, "From Nano cellulose Science towards Applications", VTT—Technical Research Center of Finland, PulpPaper 2010, Jun. 2010, Helsinki, pp. 1-24.
Herrick et al. "Microfibrillated Cellulose: Morphology and Accessibility," Journal of Applied Polymer Science, Applied Polymer Symposium 37—Proceedings of the Ninth Cellulose Conference II. Symposium on Cellulose and Wood as Future Chemical Feedstocks and Sources of Energy, and General Papers, John Wiley & Sons, Inc., May 24-27, 1982, 11 pages.
Herrick et al., "Microfibrillated, Cellulose: Morphology and Accessibility," Journal of Applied Polymer Science: Applied Polymer Symposium (1983) 37 pp. 797-813.
http://puu.tkk.fi/em/research/research_groups/chemical_pupling_and_wood_refinery/seminar_presentations/43 knuts_100609_1aitoksen_sisainen_seminaariesitys.pdf;Knuts, M.SC. Aaro, "Process installation and optimization to D refine and produce NFC materials." pp. 1-9, 2010.
Hubbe et al. "Mini-encyclopedia of papermaking wet-end chemistry." NC State University Internet Citation, Aug. 17, 2010, p. 1.
Hubbe et al., "What happens to cellulosic fibers during papermaking and recycling" A Review. Bioresources 2(4), 739-788. (2007).
Hult et al., "Cellulose Fibril Aggregation—An Inherent Property of Kraft Pulps," Polymer 42 (2001) pp. 3309-3314.
Indian Examination Report dated Aug. 24, 2017 for Indian Patent Application No. 2046/MUMNP/2011, 7 pages.
Indian Examination Report dated Jun. 12, 2017 from Indian Patent Application No. 1474/MUMNP/2011, 12 pages.
Indonesian Office Action dated Apr. 18, 2017 from Indonesian Patent Application No. WO 00 2012 04369, 4 pages.
Indonesian Office Action dated Mar. 10, 2016 from Indonesian Patent Application No. W00201103469, 2 pages.
Indonesian Office Action dated Oct. 13, 2015 from Indonesian Patent Application No. W00201103474, 4 pages.
Indonesian Office Action dated Feb. 13, 2018 for Indonesian Patent Application No. W00201204368, 4 pages.
Innventia, "Processes for Nano cellulose," http://www.innventia.com/templates/STFIPage_ 9108.aspx, 2011, 1 page.
International Preliminary Report on Patentability dated Oct. 30, 2012 for PCT/EP2011/056542, 6 pages.
International Report on Patentability for International Patent Application No. PCT/EP2010/054233, dated Oct. 2, 2011, 9 pages.
International Report on Patentability for International Patent Application No. PCT/EP2011/056540, dated Oct. 30, 2012, 6 pages.
International Preliminary Report on Patentability and the Written Opinion dated Oct. 4, 2011 from PCT Patent Application No. PCT/EP2010/054231, 8 pages.
International Search Report and Written Opinion dated Jun. 22, 2011 for International Application No. PCT/EP2011/056540, 11 pages.
International Search Report and Written Opinion for International Application No. PCT/EP2011/056542, dated May 27, 2011, 9 pages.
International Search Report and Written Opinion dated Sep. 3, 2010 for International Application No. PCT/EP2010/054233, 12 pages.
International Search Report and Written Opinion dated Jun. 7, 2010 for International Application No. PCT/EP2010/054231, 12 pages.
Ioelovich and Figovsky, "Structure and Properties of Nanoparticles Used in Paper Compositions," Mechanics of Composite Materials, vol. 46, No. 4, 2010, pp. 435-442.
Ioelovich, Michael, "Cellulose as a Nanostructured Polymer: A Short Review." BioResources, vol. 3, No. 4, 2008, pp. 1403-1418.
Iwamoto, et al. "Nano-fibrillation of pulp fibers for the processing of transparent nanocomposites", Applied Physics A, vol. 89, 2007, pp. 461-466.
Iwamoto, et al. "Optically transparent composites reinforced with plant fiber-based nanofibers", Applied Physics A, vol. 81, 2005, pp. 1109-1112.
Janardhnan, et al. "Isolation of Cellulose Microfibrils—An Enzymatic Approach", BioResources, vol. 1, No. 2, 2006, pp. 176-188.
Japanese Notice of Rejection dated Mar. 31, 2015 for Japanese Patent Application No. 2013-506620, 9 pages.
Japanese Office Action dated Apr. 14, 2015 for Japanese Patent Application No. 2012-502647, 7 pages.
Japanese Office Action dated Apr. 15, 2014 for Japanese Patent No. 2012-502647, 12 pages.
Japanese Office Action dated Dec. 1, 2015 for Japanese Patent Application No. 2013-506621, 5 pages.
Japanese Office Action dated Dec. 8, 2015 for Japanese Patent Application No. 2014-248634, 8 pages.
Japanese Office Action dated Jan. 28, 2014 for Japanese Patent Application No. 2012-502646.
Japanese Office Action dated Mar. 31, 2015 for Japanese Patent Application No. 2013-506621, 7 pages.
Japanese Office Action dated Nov. 29, 2016 for Japanese Patent Application No. 2015-159928, 11 pages.
Japanese Office Action dated Nov. 7, 2017 for Japanese Patent Application No. 2016-234040, 11 pages.
Japanese Office Action dated Oct. 20, 2015 for Japanese Patent No. 2012-502647, 3 pages.
Japanese Office Action for corresponding Japanese Patent Application No. 2014-248634 dated Jan. 9, 2018, 11 pages.
Japanese Office Action for corresponding Japanese Patent Application No. 2014-248634 dated Mar. 10, 2017, 6 pages.
Kang, Taegeun, "Role of External Fibrillation in Pulp and Paper Properties," Doctoral Thesis, Helsinki University of Technology, Laboratory of Paper and Printing Technology Reports, Series A28, Espoo 2007, 50 pages.
Klemm et al., "Cellulose: Fascinating Biopolymer and Sustainable Raw Material." Angew Chem. Int Ed. 2005 vol. 44, pp. 3358-3393.
Klemm, et al. "Nanocelluloses as Innovative Polymers in Research and Application", Adv. Polymer Science, vol. 205, 2006, pp. 49-96.
Klungness, et al. "Fiber-Loading: A Progress Report", TAPPI Proceedings, 1994 Recycling Symposium, pp. 283-290.
Korean Notice of Rejection for Korean Patent Application No. 10-2015-7030983 dated Jul. 29, 2016, 16 pages.
Korean Office Action and Notice Requesting Consultation, dated Nov. 25, 2016 for Korean Patent Application No. 10-2011-7025315, 10 pages.
Korean Office Action dated Aug. 11, 2017 for Korean Patent Application No. 10-2017-7017876, 5 pages.
Korean Office Action dated Feb. 20, 2017 for Korean Patent Application No. 10-2016-7030178, 7 pages.
Korean Office Action dated Jan. 27, 2016 for Korean Patent Application No. 10-2011-7025315, 13 pages.
Korean Office Action dated Jul. 28, 2016 for Korean Patent Application No. 10-2011-7025315, 7 pages.
Korean Office Action dated Jul. 29, 2016 for Korean Patent Application No. 10-2012-7030761, 13 pages.
Korean Office Action dated Mar. 28, 2016 for Korean Patent Application No. 10-2011-7025318, 12 pages.
Brazilian Examination Report for Brazilian Patent Application No. PI 1013180-9, dated Oct. 16, 2018, 6 pages.
Chinese Second Office Action dated Sep. 12, 2018 for Chinese Patent Application No. 201610882363.1, 6 pages.
Daiyong et al., "Advances in Cellulose Chemistry," J. of Chemical Industry and Engineering, vol. 57, No. 8, (2006), pp. 1782-1791.

(56) References Cited

OTHER PUBLICATIONS

Daiyong, Ye, "Preparation of Nanocellulose," Progress in Chemistry, vol. 19, No. 10, (2007), pp. 1568-1575.
European Office Action for corresponding European Patent Application No. 141754 71.3 dated May 17, 2018, 3 pages.
Indian Examination Report dated Jun. 5, 2018 for Indian Patent Application No. 2018/MUMNP/2011, 7 pages.
Indian Examination Report dated Jun. 12, 2018 for Indian Patent Application No. 2404/MUMNP/2012, 6 pages.
Indian Examination Report dated Jun. 29, 2018 for Indian Patent Application No. 2424/MUMNP/2012, 5 pages.
Japanese Official Action dated May 22, 2018 for Japanese Patent Application No. 2016-234040, 4 pages.
Ling-ling and Xiao-quan, "Research Status of the Nano-Crystalline Cellulose," J. of Cellulose Science and Technology, vol. 16, No. 2, (2008), 18 pages.
"Packaging Technical Manual," Edited by Japan Packaging Technology Association (1994), 12 pages.
Response by Opponent to Notice of Appeal Against EP2236664, dated Jul. 3, 2018, submitted to the European Patent Office, 15 pages.
Opponent Submission Preparation Oral Proceedings Against EP2236664, dated Nov. 13, 2018, 5 pages.
Russian Search Report dated Apr. 25, 2018 for Russian Patent Application No. 2014130594, 4 pages.
U.S. Final Office Action for U.S. Appl. No. 14/474,705, dated Sep. 27, 2018, 9 pages.
U.S. Final Office Action for U.S. Appl. No. 13/640,513, dated Oct. 10, 2018, 13 pages.
U.S. Non-Final Office Action for U.S. Appl. No. 16/040,652, dated Nov. 13, 2018, 15 pages.
European Office Action for European Patent Application No. 141754 71.3, dated Oct. 15, 2018, 4 pages.

* cited by examiner

PROCESS FOR THE PRODUCTION OF GEL-BASED COMPOSITE MATERIALS

CROSS-REFERENCE TO RELATED APPLICATIONS

This application is a U.S. national phase of PCT Application No. PCT/EP2011/056540, filed Apr. 26, 2011, which claims priority to European Application No. 10161173.9, filed Apr. 27, 2010 and U.S. Provisional Application No. 61/343,774, filed May 4, 2010.

The present invention relates to a process for the production of gel-based composite materials, the materials obtained by this process as well as the use thereof in several applications.

A composite material is basically a combination of two or more materials, each of which retains its own distinctive properties. The resulting material has characteristics that are not characteristic of the components in isolation. Most commonly, composite materials have a bulk phase, which is continuous, called the matrix; and a dispersed, non-continuous, phase called the reinforcement. Some other examples of basic composites include concrete (cement mixed with sand and aggregate), reinforced concrete (steel rebar in concrete), and fibreglass (glass strands in a resin matrix).

The following are some of the reasons why composites are selected for certain applications:
High strength to weight ratio (low density high tensile strength)
High creep resistance
High tensile strength at elevated temperatures
High toughness Typically, reinforcing materials are strong, while the matrix is usually a ductile, or tough, material. If the composite is designed and fabricated correctly, it combines the strength of the reinforcement with the toughness of the matrix to achieve a combination of desirable properties not available in any single conventional material. For example: polymer/ceramic composites have a greater modulus than the polymer component, but aren't as brittle as ceramics.

Since the reinforcement material is of primary importance in the strengthening mechanism of a composite, it is convenient to classify composites according to the characteristics of the reinforcement. The following three categories are commonly used:
a) "fibre reinforced", wherein the fibre is the primary load-bearing component.
b) "particle reinforced", wherein the load is shared by the matrix and the particles.
c) "dispersion strengthened", wherein the matrix is the major load-bearing component.
d) "structural composites", wherein the properties depend on the constituents, and the geometrical design.

Generally, the strength of the composite depends primarily on the amount, arrangement and type of fibre (or particle) reinforcement in the resin. In addition, the composite is often formulated with fillers and additives that change processing or performance parameters.

Advanced composites utilize a combination of resins and fibres, customarily carbon graphite, kevlar, or fibreglass with an epoxy resin. The fibres provide the high stiffness, while the surrounding polymer resin matrix holds the structure together. The fundamental design concept of composites is that the bulk phase accepts the load over a large surface area, and transfers it to the reinforcement material, which can carry a greater load. These materials were first developed for use in the aerospace industry because for certain application they have a higher stiffness to weight or strength-to-weight ratio than metals. This means metal parts can be replaced with lighter weight parts manufactured from advanced composites.

Thus, in the prior art it is well-known to implement polymers and the like in composites, which however are relatively expensive and environmentally unfriendly. Furthermore, the addition of fillers as mentioned generally requires surface treatment, implying high processing costs.

Thus, there is still a need for the provision of cost-efficient and environmentally friendly composite materials.

Looking for a solution of this object, several materials were investigated, inter alia, cellulose and calcium carbonate.

Cellulose is the structural component of the primary cell wall of green plants and is the most common organic compound on Earth. It is of high interest in many applications and industries.

Cellulose pulp as a raw material is processed out of wood or stems of plants such as hemp, linen and manila. Pulp fibres are built up mainly from cellulose and other organic components (hemicellulose and lignin). The cellulose macromolecules (composed of 1-4 glycosidic linked β-D-Glucose molecules) are linked together by hydrogen bonds to form a so called primary fibril (micelle) which has crystalline and amorphous domains. Several primary fibrils (around 55) form a so called microfibril. Around 250 of these microfibrils form a fibril.

The fibrils are arranged in different layers (which can contain lignin and/or hemicellulose) to form a fibre. The individual fibres are bound together by lignin as well.

When fibres become refined under applied energy they become fibrillated as the cell walls are broken and torn into attached strips, i.e. into fibrils. If this breakage is continued to separate the fibrils from the body of the fibre, it releases the fibrils. The breakdown of fibres into microfibrils is referred to as "microfibrillation". This process may be continued until there are no fibres left and only fibrils of nano size (thickness) remain.

If the process goes further and breaks these fibrils down into smaller and smaller fibrils, they eventually become cellulose fragments or nano-fibrillar gels. Depending on how far this last step is taken some nano-fibrils may remain amongst the nano-fibrillar gel. The breakdown to primary fibrils may be referred to as "nano-fibrillation", where there may be a smooth transition between the two regimes. The primary fibrils form in an aqueous environment a gel (meta stable network of primary fibrils) which may be referred to as "nano-fibrillar gel". The gel formed from the nano-fibrils can be considered to contain nanocellulose.

Nano-fibrillar gels are desirable as they usually contain very fine fibrils, considered to be constituted in part of nanocellulose, showing a stronger binding potential to themselves, or to any other material present, than do fibrils which are not so fine or do not exhibit nanocellulosic structure.

From unpublished European patent application No. 09 156 703.2, nano-fibrillar cellulose gels are known. However, there is no teaching with respect to the formation of composite materials.

It has now been found that such cellulose gels can be formed into composite materials, which can be produced easier/faster by the addition of fillers and/or pigments to such gels, and result in an improved runnability, and which are environmentally friendlier compared with many other composite materials.

Thus, the above problem is solved by a process for the production of composite materials comprising nano-fibrillar cellulose gels, which is characterized by the following steps:
a) providing cellulose fibres;
b) providing at least one filler and/or pigment;
c) combining the cellulose fibres of step a) and the at least one filler and/or pigment of step b);
d) fibrillating the cellulose fibres in the presence of the at least one filler and/or pigment until a gel is formed;
e) providing at least one further filler and/or pigment;
f) combining the gel of step d) with the at least one further filler and/or pigment of step e).

Nano-fibrillar cellulose in the context of the present invention means fibres, which are at least partially broken down to primary fibrils. If these primary fibrils are in an aqueous environment, a gel (meta stable network of primary fibrils considered in the limit of fineness to be essentially nanocellulose) is formed, which is designated as "nano-fibrillar gel", wherein there is a smooth transition between nano fibres and nano-fibrillar gel, comprising nano-fibrillar gels containing a varying extent of nano-fibrils, all of which are comprised by the term nano-fibrillar cellulose gels according to the present invention.

In this respect, fibrillating in the context of the present invention means any process which predominantly breaks down the fibres and fibrils along their long axis resulting in the decrease of the diameter of the fibres and fibrils, respectively.

According to the process of the present invention, the fibrillation of cellulose fibres in the presence of at least one filler and/or pigment provides a nano-fibrillar cellulose gel. The fibrillation is performed until the gel is formed, wherein the formation of the gel is verified by the monitoring of the viscosity in dependence of the shearing rate. Upon step-wise increase of the shearing rate a certain curve reflecting a decrease of the viscosity is obtained. If, subsequently the shearing rate is step-wise reduced, the viscosity increases again, but the corresponding values over at least part of the shear rate range as shearing approaches zero are lower than when increasing the shearing rate, graphically expressed by a hysteresis manifest when the viscosity is plotted against the shearing rate. As soon as this behaviour is observed, a nano-fibrillar cellulose gel according to the present invention is formed. Further details with respect to the production of the nano-fibrillar cellulose gel can be taken from unpublished European patent application No. 09 156 703.

Cellulose fibres, which can be used in the process of the present invention may be such contained in natural, chemical, mechanical, chemimechanical, thermomechanical pulps. Especially useful are pulps selected from the group comprising eucalyptus pulp, spruce pulp, pine pulp, beech pulp, hemp pulp, cotton pulp, bamboo pulp, bagasse, and mixtures thereof. In one embodiment, all or part of this cellulose fibre may be issued from a step of recycling a material comprising cellulose fibres. Thus, the pulp may also be recycled and/or deinked pulp.

The size of the cellulose fibres in principle is not critical. Useful in the present invention generally are any fibres commercially available and processable in the device used for their fibrillation. Depending on their origin, cellulose fibres may have a length of from 50 mm to 0.1 µM. Such fibres, as well as such having a length of preferably 20 mm to 0.5 µm, more preferably from 10 mm to 1 mm, and typically from 2 to 5 mm, can be advantageously used in the present invention, wherein also longer and shorter fibres may be useful.

It is advantageous for the use in the present invention that the cellulose fibres are provided in the form of a suspension, especially an aqueous suspension. Preferably, such suspensions have a solids content of from 0.2 to 35 wt-%, more preferably 0.25 to 10 wt-%, even more preferably 0.5 to 5 wt-%, especially 1 to 4 wt-%, most preferably 1.3 to 3 wt-%, e.g. 1.5 wt-%.

The at least one filler and/or pigment of steps b) and e) are independently selected from the group comprising precipitated calcium carbonate (PCC); natural ground calcium carbonate (GCC); surface modified calcium carbonate; dolomite; talc; bentonite; clay; magnesite; satin white; sepiolite, huntite, diatomite; silicates; and mixtures thereof.

Precipitated calcium carbonate, which may have vateritic, calcitic or aragonitic crystal structure, and/or natural ground calcium carbonate, which may be selected from marble, limestone and/or chalk, are especially preferred.

In a special embodiment, the use of ultrafine discrete prismatic, scalenohedral or rhombohedral precipitated calcium carbonate may be advantageous.

The filler(s) and/or pigment(s) can be provided in the form of a powder, although they are preferably added in the form of a suspension, such as an aqueous suspension. In this case, the solids content of the suspension is not critical as long as it is a pumpable liquid.

In a preferred embodiment, the filler and/or pigment particles of step b) have a median particle size of from 0.01 to 15 µm, preferably 0.1 to 10 µm, more preferably 0.3 to 5 µm, especially from 0.5 to 4 µm and most preferably 0.7 to 3.2 µm, e.g. 2 µm.

For the determination of the weight median particle size $d_{50}$, for particles having a $d_{50}$ greater than 0.5 µm, a Sedigraph 5100 device from the company Micromeritics, USA was used. The measurement was performed in an aqueous solution of 0.1 wt-% $Na_4P_2O_7$. The samples were dispersed using a high-speed stirrer and ultrasound. For the determination of the volume median particle size for particles having a $d_{50} \leq 500$ nm, a Malvern Zetasizer Nano ZS from the company Malvern, UK was used. The measurement was performed in an aqueous solution of 0.1 wt % $Na_4P_2O_7$. The samples were dispersed using a high-speed stirrer and ultrasound.

It has turned out especially advantageous, if the filler(s) and/or pigment(s) added in step e) is a rather fine product in terms of the particle size, and especially preferably comprises at least a fraction of particles having a median diameter $d_{50}$ in the nanometer range, contrary to the pigment(s) and/or filler(s) used in the gel formation, which are rather coarse ones.

Thus, it is furthermore preferred that the filler and/or pigment particles of step e) have a median particle size of from 0.01 to 5 µm, preferably 0.05 to 1.5 µm, more preferably 0.1 to 0.8 µm and most preferably 0.2 to 0.5 µm, e.g. 0.3 µm, wherein the particle size is determined as mentioned above.

The filler(s) and/or pigments) may be associated with dispersing agents such as those selected from the group comprising homopolymers or copolymers of polycarboxylic acids and/or their salts or derivatives such as esters based on, e.g., acrylic acid, methacrylic acid, maleic acid, fumaric acid, itaconic acid; e.g. acryl amide or acrylic esters such as methylmethacrylate, or mixtures thereof; alkali polyphosphates, phosphonic-, citric- and tartaric acids and the salts or esters thereof; or mixtures thereof.

The combination of fibres and at least one filler and/or pigment of steps b) and/or e) can be carried out by adding the filler and/or pigment to the fibres in one or several steps.

As well, the fibres can be added to the filler and/or pigment in one or several steps. The filler and/or pigment of step b) as well as the fibres can be added entirely or in portions before or during the fibrillating step. However, the addition before fibrillating is preferred.

During the fibrillation process, the size of the filler(s) and/or pigment(s) as well as the size of the fibres can change.

Preferably, the weight ratio of fibres to filler(s) and/or pigment(s) of step b) on a dry weight basis is from 1:33 to 10:1, more preferably 1:10 to 7:1, even more preferably 1:5 to 5:1, typically 1:3 to 3:1, especially 1:2 to 2:1 and most preferably 1:1.5 to 1.5:1, e.g. 1:1.

The dosage of filler and/or pigment in step b) may be critical. If there is too much of the filler and/or pigment, this may influence the formation of the gel. Thus, if no gel formation is observed in specific combination, it might be necessary to reduce the amount of filler and/or pigment.

Furthermore, in one embodiment, the combination is stored for 2 to 12 hours, preferably 3 to 10 hours, more preferably 4 to 8 hours, e.g. 6 hours, prior to fibrillating it, as this ideally results in swelling of the fibres facilitating the fibrillation.

Fibre swelling may be facilitated by storage at increased pH, as well as by addition of cellulose solvents like e.g. copper(II)ethylenediamine, iron-sodium-tartrate or lithium-chlorine/dimethylacetamine, or by any other method known in the art.

Fibrillating is carried out by means of any device useful therefore. Preferably the device is a homogenizer. It may also be an ultra fine friction grinder such as a Supermasscolloider from Masuko Sangyo Co. Ltd, Japan or one as described in U.S. Pat. No. 6,214,163 or 6,183,596.

Suitable for the use in the present invention are any commercially available homogenizers, especially high pressure homogenizers, wherein the suspensions are pressed under high pressure through a restricted opening, which may comprise a valve, and are discharged from the restricted opening at high pressure against a hard impact surface directly in front of the restricted opening. The pressure may be generated by a pump such as a piston pump, and the impact surface may comprise an impact ring extending around the annular valve opening. An example for an homogenizer which can be used in the present invention is Ariete NS2006L of GEA Niro Soavi. However, inter alia, also homogenizers such as of the APV Gaulin Series, HST HL Series or the Alfa Laval SHL Series can be used.

Furthermore, devices such as ultra-fine friction grinders, e.g. a Supermasscolloider, can be advantageously used in the present invention.

It is furthermore preferred that the weight ratio of fibres to filler and/or pigment of step e) on a dry weight basis is from 1:9 to 99:1, preferably from 1:3 to 9:1, more preferably from 1:2 to 3:1, e.g. 2:1.

Regarding the total content of filler and/or pigment it is especially preferred that the filler and/or pigment of steps b) and e) are present in an amount of from 10 wt-% to 95 wt-%, preferably from 15 wt-% to 90 wt-%, more preferably from 20 to 75 wt-%, even more preferably from 25 wt-% to 67 wt-%, especially from 33 to 50 wt.-% on a dry weight basis of the composite material.

The combination of the gel of step d) with the at least one further filler and/or pigment of step e) may be carried out just by mixing the combination, e.g. by means of a spatula. Furthermore, it may advantageous to mix the components by means of a stirrer with a mounted dissolver disc.

Subsequently the resulting combination may be dewatered. In this respect, generally any commonly used method of dewatering known to the person skilled in the art, may be used, such as e.g. heat drying, pressure drying, vacuum drying, freeze drying, or drying under supercritical conditions. The dewatering step may be carried out in well-known devices such as in a filter press, e.g. as described in the Examples. Generally, other methods that are well known in the field of moulding of aqueous systems can be applied to obtain the inventive composites.

The use of the nano-fibrillar cellulose gels as defined above for the production of a compacted composite material is a further aspect of the invention, wherein the gel is combined with at least one further filler and/or pigment and the resulting combination is dewatered as described in detail above.

Another aspect of the present invention is the composite material obtained by the process according to the invention, or by the use of the nano-fibrillar cellulose gels for the production of the composite material as mentioned.

The composite material can be advantageously used in applications such as in plastics, paints, rubber, concrete, ceramics, pannels, housings, foils, films, coatings, extrusion profiles, adhesives, food, or in wound-healing applications, and can readily replace certain materials such as plastics used as e.g. construction material, packaging, etc.

EXAMPLES

Material

OC-GCC: Omyacarb® 10-AV available from Omya AG; Fine calcium carbonate powder manufactured from a high purity, white marble; the weight median particle size $d_{50}$ is 10 μm measured by Malvern Mastersizer X.

HO-ME: Hydrocarb® HO-ME available from Omya AG; Selected, natural ground calcium carbonate (marble), microcrystalline, rhombohedral particle shape of high fineness in the form of a pre-dispersed slurry (solids content 62 wt-%); the weight median particle size $d_{50}$ is 0.8 μm measured by Sedigraph 5100.

Nano-GCC: Natural ground calcium carbonate (marble from Vermont); dispersed slurry (solids content 50 wt-%); the volume median particle size is $d_{50}$ of 246 nm measured by Malvern Zetasizer Nano ZS.

Pulp: Eucalyptus pulp with 25° SR.

Gel Formation 120 g Eucalyptus pulp in the form of dry mats was torn into pieces and mixed with 5880 g tap water and the respective amount of OC-GCC (see Table 1) was added. The resulting mixture was stirred for at least 15 minutes using a Pendraulik (dissolver disk) at 4000 rpm. The fibrillar content of the formulations was 3 wt %.

The resulting mixtures subsequently were fibrillated in an ultra-fine friction grinder (Supermasscolloider from Masuko Sangyo Co. Ltd, Japan (Model MKCA 6-2) in single passes at a "gap" of −50 μm (dynamic O-point) with the following setup:

5 passes at 2500 rpm,
2 passes at 2000 rpm,
2 passes at 1500 rpm,
2 passes at 1000 rpm,
2 passes at 750 rpm,
2 passes at 500 rpm.

The grinding stones were silicon carbide with a grit class of 46 (grit size 297-420 μm).

TABLE 1

Composition and characteristics of the gel used for compact formulations

| Sample | Parts GCC on pulp fibres [dry/dry] | Energy input [MWh/dmt] | Brookfield viscosity at 2 wt-% solids content [MPa · s] |
|---|---|---|---|
| 1 | 1 | 5.38 | 1612 |

Production of Formulations

In order to obtain and test compacts of the nano cellulosic gels, the following formulations for the specimen production were produced according to Table 2.

TABLE 2

Composition of compact formulations

| Sample | GCC in gel formulation [parts dry on fibres dry] (wt % on overall formulation) | Additional GCC [parts dry on fibres dry] (wt % on overall formulation) | Total GCC in formulation [parts dry on fibres dry] (wt % on overall formulation) |
|---|---|---|---|
| 1 | 1 p (50 wt %) | 0 p (0 wt %) | 1 p (50 wt %) |
| 2 (sample 1 + 2 p Nano) | 1 p (25 wt %) | 2 p nano GCC (50 wt %) | 3 p (75 wt %) |
| 3 (sample 1 + 2 p HO-ME (disp.)) | 1 p (25 wt %) | 2 p HO-ME (50 wt %) | 3 p (75 wt %) |

The gel of sample 1 was mixed with the corresponding amount of additional GCC as mentioned in Table 2 and blended by hand with a spatula.

Subsequently, the formulations were put into a small filter press (filter paper of Whatman Schleicher & Schuell, 589/2, white ribbon; filter press: fann filter press, series 3000, fann instrument company, Houston Tex., USA) in such amounts that a final thickness of the specimen of about 3 mm (calculated via densities) was achieved. A PMMA disc (thickness: 10 mm, diameter: 78 mm (fitting the inner diameter of the filter press) was placed on top of the formulation which again was covered by additional material of the same formulation (around 10-20 wt % of the amount of formulation already present).

The filter press then was closed and the following pressure profile was applied:
15 min at 1 bar,
120 min at 4 bar,
45 min at 6 bar.

Subsequently, the "semi-dry" disc (solids content: about 50 wt %) was taken out of the filter press and cut into five identical rectangles (40 mm×10 mm). These rectangles were placed between two filter papers and two aluminium plates weighted with steel balls (about 3000 g), and dried in an oven at about 80° C. over night.

The invention claimed is:

1. A process for producing a composite material comprising the steps of:
   (a) providing cellulose fibres, wherein the cellulose fibres of step (a) are selected from *eucalyptus* pulp, spruce pulp, pine pulp, beech pulp, hemp pulp, cotton pulp, bamboo pulp, bagasse, recycled pulp, deinked pulp, or any mixture thereof;
   (b) providing at least one filler comprising calcium carbonate, wherein the filler of step (b) consists of particles having a median particle size of from 0.5 to 4 μm;
   (c) combining the cellulose fibres of step (a) and the at least one filler of step (b) at a weight ratio of fibres to filler on a dry weight basis of from 1:33 to 10:1 by adding the fibres and at least one filler entirely or in portions before or during the fibrillating step (d);
   (d) fibrillating the cellulose fibres in an aqueous environment in the presence of the at least one filler from step (c) until a nano-fibrillar gel is formed; wherein the formation of the gel is verified by monitoring the viscosity of the mixture in dependence of the shearing rate, wherein the viscosity decrease of the mixture upon step-wise increase of the shearing rate is stronger than the corresponding viscosity increase upon subsequent step-wise reduction of the shearing rate over at least part of the shear rate range as shearing approaches zero;
   (e) providing at least one further filler, wherein the at least one further filler of step (e) consists of particles having a median particle size of from 0.01 to 15 μm; and
   (f) combining the nano-fibrillar gel obtained in step (d) with the at least one further filler from of step (e), wherein the combination of the gel and the at least one further filler from step (f) is subjected to dewatering to obtain a compacted composite material.

2. The process according to claim 1, wherein the cellulose fibres of step (a) are provided in the form of a suspension.

3. The process according to claim 1, wherein the cellulose fibres of step (a) are provided in the form of a suspension at a solids content of from 0.2 to 35 wt %.

4. The process according to claim 1, wherein the cellulose fibres of step (a) are provided in the form of a suspension at a solids content of from 1 to 4 wt %.

5. The process according to claim 1, wherein the filler of step (e) is precipitated calcium carbonate (PCC), natural ground calcium carbonate (GCC), surface modified calcium carbonate, dolomite, talc, bentonite, clay, magnesite, satin white, sepiolite, huntite, diatomite, a silicate, or any mixture thereof.

6. The process according to claim 1, wherein the filler of steps (b) and (e) are independently selected from precipitated calcium carbonate having vateritic, calcitic or aragonitic crystal structure, ultrafine discrete prismatic, scalenohedral or rhombohedral precipitated calcium carbonate, natural ground calcium carbonate, marble, limestone, chalk, or any mixture thereof.

7. The process according to claim 1, wherein the at least one further filler of step (e) consists of particles having a median particle size of from 0.01 to 5 μm.

8. The process according to claim 1, wherein the at least one further filler of step (e) consists of particles having a median particle size of from 0.05 to 1.5 μm.

9. The process according to claim 1, wherein the at least one further filler of step (e) consists of particles having a median particle size of from 0.1 to 0.8 μm.

10. The process according to claim 1, wherein the filler of steps (b) and/or (e) is associated with a dispersing agent selected from homopolymers or copolymers of polycarboxylic acids and/or their salts or derivatives or esters thereof; esters based on acrylic acid, methacrylic acid, maleic acid, fumaric acid, itaconic acid; acryl amide or acrylic esters, methylmethacrylate, or any mixture thereof; alkali polyphosphates, phosphonic-, citric- and tartaric acids and the salts or esters thereof; or any mixture thereof.

11. The process according to claim 1, wherein the combination of fibres and of at least one filler of step (b) is carried out by adding the filler to the fibres, or the fibres to the filler, in one or several steps.

12. The process according to claim 1, wherein the weight ratio of fibres to filler in step (c) on a dry weight basis is from 1:10 to 7:1.

13. The process according to claim 1, wherein the weight ratio of fibres to filler in (step c) on a dry weight basis is from 1:2 to 2:1.

14. The process according to claim 1, wherein the fibrillating is carried out with a homogenizer or a friction grinder.

15. The process according to claim 1, wherein the weight ratio of fibres from step (a) to filler of step (e) on a dry weight basis is from 1:9 to 99:1.

16. The process according to claim 1, wherein the weight ratio of fibres from step (a) to filler of step (e) on a dry weight basis is from 1:3 to 9:1.

17. The process according to claim 1, wherein the weight ratio of fibres from step (a) to filler of step (e) on a dry weight basis is from 1:2 to 3:1.

18. The process according to claim 1, wherein the total content of filler of steps (b) and (e) on a dry weight basis of the composite material is from 10 wt-% to 95 wt-%.

19. The process according to claim 1, wherein the total content of filler of steps (b) and (e) on a dry weight basis of the composite material is from 20 wt-% to 75 wt-%.

20. The process according to claim 1, wherein the total content of filler of steps (b) and (e) on a dry weight basis of the composite material is from 25 wt-% to 67 wt-%.

21. The process according to claim 1, wherein the total content of filler of steps (b) and (e) on a dry weight basis of the composite material is from 33 wt-% to 50 wt-%.

22. A process for producing a composite material comprising the steps of:
 (a) providing cellulose fibres;
 (b) providing at least one filler comprising calcium carbonate and one or more of dolomite, talc, bentonite, clay, magnesite, satin white, sepiolite, huntite, diatomite, and a silicate;
 (c) combining the cellulose fibres of step (a) and the at least one filler of step (b) at a weight ratio of fibres to filler on a dry weight basis of from 1:33 to 10:1 by adding the fibres and at least one filler entirely or in portions before or during the fibrillating step (d);
 (d) fibrillating the cellulose fibres in an aqueous environment in the presence of the at least one filler from step (c) until there are no fibres left and a nano-fibrillar gel is formed in an aqueous environment to obtain a fibrillation product;
 wherein the formation of the gel is verified by monitoring the viscosity of the mixture in dependence of the shearing rate, wherein the viscosity decrease of the mixture upon step-wise increase of the shearing rate is stronger than the corresponding viscosity increase upon subsequent step-wise reduction of the shearing rate over at least part of the shear rate range as shearing approaches zero;
 (e) providing at least one further filler, wherein the at least one further filler consists of particles having a median particle size of from 0.01 to 15 µm; and
 (f) combining the nano-fibrillar gel in step (d) with the at least one further filler of step (e), wherein the combination of the gel and the at least one further filler from step (f) is subjected to dewatering to obtain a compacted composite material.

\* \* \* \* \*